United States Patent
Friese et al.

(10) Patent No.: US 8,729,292 B2
(45) Date of Patent: May 20, 2014

(54) METHOD FOR REGENERATION OF RAW ESTER

(75) Inventors: Katrin Friese, Mannheim (DE); Walter Disteldorf, Wachenheim (DE); Jarren Peters, Mannheim (DE); Günther Golfier, Frankenthal (DE)

(73) Assignee: BASF SE, Ludwigshafen (DE)

( * ) Notice: Subject to any disclaimer, the term of this patent is extended or adjusted under 35 U.S.C. 154(b) by 285 days.

(21) Appl. No.: 13/140,239

(22) PCT Filed: Dec. 15, 2009

(86) PCT No.: PCT/EP2009/067178
§ 371 (c)(1),
(2), (4) Date: Jun. 16, 2011

(87) PCT Pub. No.: WO2010/076193
PCT Pub. Date: Jul. 8, 2010

(65) Prior Publication Data
US 2011/0251419 A1    Oct. 13, 2011

(30) Foreign Application Priority Data
Dec. 16, 2008 (EP) .................................... 08171800

(51) Int. Cl.
*C07C 67/48* (2006.01)
(52) U.S. Cl.
USPC .................................. 560/78; 560/98; 560/99
(58) Field of Classification Search
USPC ............................................ 560/78, 98, 99
See application file for complete search history.

(56) References Cited

U.S. PATENT DOCUMENTS

| | | | | |
|---|---|---|---|---|
| 6,310,235 | B1 * | 10/2001 | Gick | 560/99 |
| 6,916,950 | B2 * | 7/2005 | Gubisch et al. | 560/204 |
| 7,291,748 | B2 * | 11/2007 | Storzum et al. | 560/76 |
| 2006/0270868 | A1 | 11/2006 | Compton et al. | |

FOREIGN PATENT DOCUMENTS

| | | |
|---|---|---|
| DE | 1945359 A1 | 3/1971 |
| DE | 2330435 A1 | 1/1975 |
| EP | 0439722 A1 | 8/1991 |
| EP | 1300388 A2 | 4/2003 |

OTHER PUBLICATIONS

U.S. Appl. No. 13/140,256, filed Jun. 16, 2011, Disteldorf et al.
U.S. Appl. No. 13/140,274, filed Jun. 16, 2011, Peters et al.
Cornils, B., et al., "Applied Homogeneous Catalysis with Organometallic Compounds: A Comprehensive Handbook in Two Volumes", Dimerization and Codimerization, Verlag Chemie, (1996), pp. 261-263.
Friedlander, R., et al., "Make plasticizer olefins via n-butene dimerization", Hydrocarbon Processing, vol. 65, (1986), pp. 31-33.
International Search Report for PCT/EP2009/067178, mailing date Jun. 10, 2010.
International Preliminary Report on Patentability for PCT/EP2009/067178, mailing date Jun. 21, 2011.

* cited by examiner

*Primary Examiner* — Sudhakar Katakam
*Assistant Examiner* — Pancham Bakshi
(74) *Attorney, Agent, or Firm* — Novak Druce Connolly Bove + Quigg LLP

(57) ABSTRACT

The invention relates to a raw ester of an esterification reaction catalyzed by a metal-containing esterification catalyst generated by a) mixing the raw ester at a temperature T of more than 100° C. under a pressure p that is equal to or greater than the vapor pressure of water at the temperature T with an aqueous base, b) relaxing the ester-base mixture and evaporating water, c) mixing the obtained fluid phase with water forming a water-in-oil emulsion, d) distilling water out of said emulsion and e) filtering the ester. Said method results in esters having low acid value and residues accrue in easily filterable form in the solid catalyst residues.

14 Claims, 1 Drawing Sheet

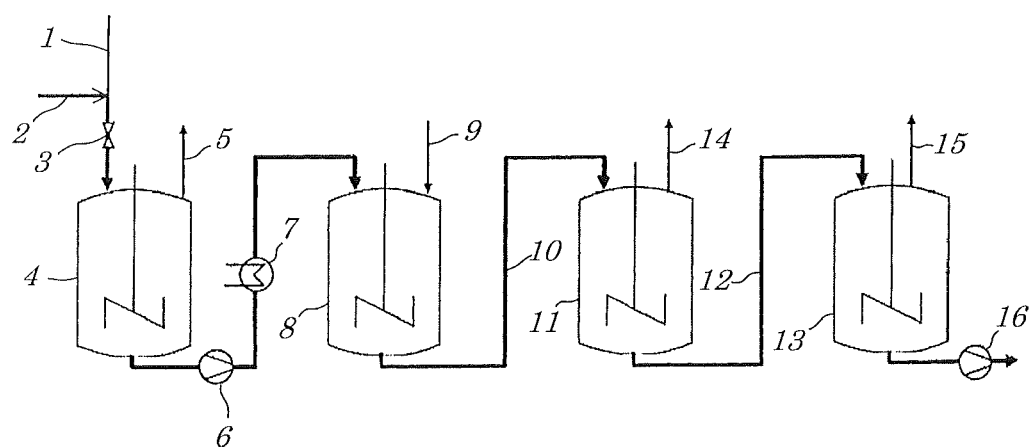

METHOD FOR REGENERATION OF RAW ESTER

CROSS-REFERENCE TO RELATED APPLICATIONS

This application is a national stage application (under 35 U.S.C. §371) of PCT/EP2009/067178, filed Dec. 15, 2009, which claims benefit of European application 08171800.9, filed Dec. 16, 2008.

BACKGROUND OF THE INVENTION

The invention relates to a process for working up a raw ester of an esterification reaction catalyzed by a metallic esterification catalyst.

Esters of phthalic acid, adipic acid, sebacic acid or maleic acid find wide use in coating resins, as constituents of paints and especially as plasticizers for polymers.

It is known that carboxylic esters can be prepared by reacting carboxylic acids with alcohols. This reaction can be carried out autocatalytically or catalytically, for example by means of Brønsted or Lewis acids. In many cases, metal compounds are used as catalysts, such as the alkoxides, carboxylates and chelate compounds of titanium, zirconium, tin, zinc and aluminum.

Even though the catalytic properties of these metallic catalysts are satisfactory, the removal of the catalyst residues from the esterification products presents difficulties. For purification, the raw esters are generally first admixed with alkali metal hydroxides to remove unconverted or incompletely converted acid (partial esters), and the free alcohols are removed by steam distillation. After brief vacuum distillation to dry the product, the catalyst residues are then removed by filtration. Since the catalyst residues are generally of slimy, gel-like consistency, filtration is usually possible only with the aid of filtration aids, for example activated carbon, wood flour or kieselguhr. Nevertheless, such a filtration is still associated with serious disadvantages: long filtration times are required and the yield of ester is reduced because large amounts of products are retained in the filtercake.

DE 194 53 59 discloses a process for working up raw plasticizers, which has the following successive steps: (i) the residue acid in the raw plasticizer is neutralized with alkaline substances (e.g. 25% sodium hydroxide solution); (ii) the free alcohols in the raw plasticizer are removed by means of steam distillation; (iii) the product is cooled to temperatures below the boiling point of the water at the particular pressure; (iv) at least 0.5% by weight of water, based on the product to be worked up, is added; (v) the mixture of water and product to be worked up is stirred intensively at temperatures below the boiling point of the water at the particular pressure for at least 15 minutes; (vi) the water added is removed by vacuum distillation; (vii) the plasticizer is filtered.

When the sodium hydroxide solution is added under the conditions specified, a significant portion of the water supplied with the aqueous alkali evaporates immediately, and so solid sodium hydroxide precipitates out. Solid sodium hydroxide reacts significantly more slowly than dissolved NaOH. In addition, the precipitation leads to deposits on pipelines and vessels, which necessitate frequent cleaning.

DE 23 30 435 describes a process for working up raw esters, in which the raw ester at a temperature of 140-250° C. is neutralized under reduced pressure simultaneously with aqueous solutions of alkali metal or alkaline earth metal hydroxide, and subjected to a steam distillation by admixing with water under reduced pressure, then dried and the solid constituents formed are filtered off. The pressure and the rate of water addition should be regulated such that the water added evaporates rapidly.

Under the process conditions under which added water evaporates immediately, solid alkali metal or alkaline earth metal hydroxide can precipitate out, which leads to the above-described disadvantages. Since solid hydroxide reacts significantly more slowly, high base excesses are sometimes required for complete neutralization.

EP 1 300 388 discloses a process for preparing carboxylic esters, wherein the excess alcohol is removed after the esterification reaction, and the raw ester thus obtained is neutralized by addition of base and is then filtered. The alcohol is removed by at least one steam distillation and the base is added during a steam distillation. The alkali is to be sprayed into the reaction mixture at the bottom. As a result of the high temperature, the water evaporates. As a result of low rates of metered addition of the alkali, side reactions, for example the hydrolysis of the esters, are to be minimized. However, this has the disadvantage of long neutralization times and/or low throughputs.

U.S. Pat. No. 5,434,294 describes a process for titanate-catalyzed preparation of plasticizer esters. The product is treated with aqueous base and then filtered with the aid of a filtration aid, such as bleaching earth, hydrotalcite or magnesium silicate.

WO 97/11048 illustrates the preparation of mixed phthalic esters. The reaction of a phthalic monoester with a polyethylene glycol monomethyl ether is catalyzed with tetraisopropyl titanium. After the reaction has ended, sodium bicarbonate solution is added dropwise. After cooling, 2% water is added, volatile compounds, such as water and solvents, are distilled off under reduced pressure, and the mixture is filtered.

DE 197 21 347 discloses a process for preparing ester plasticizers, in which a mixture of acid or acid anhydride and alcohol is first allowed to react together at from 100 to 160° C. with removal of any water formed, the reaction is conducted to completion with addition of the catalyst and by increasing the temperature up to 250° C., the reaction mixture is reacted with an aqueous alkali metal or alkaline earth metal hydroxide solution, then the excess alcohol is removed, and the remaining raw ester is dried and filtered. The alkaline treatment should appropriately immediately follow the esterification step without preceding cooling of the reaction mixture.

BRIEF SUMMARY OF THE INVENTION

It is an object of the invention to specify a process for working up a raw ester mixture, which leads with high throughput in a readily reproducible manner to esters with a low acid number, and in which the solid catalyst residues are obtained in a form which can be filtered off readily.

The object is achieved by a process for working up a raw ester of an esterification reaction catalyzed by a metallic esterification catalyst, in which a) the raw ester is admixed with an aqueous base at a temperature T of more than 100° C. under a pressure p which is equal to or greater than the vapor pressure of water at the temperature T,
b) the ester-based mixture is decompressed and water is evaporated off,
c) the resulting liquid phase is admixed with water to form a water-in-oil emulsion,
d) water is distilled out of the emulsion and
e) the ester is filtered.

The process according to the invention comprises several steps: a neutralization under pressure with subsequent decompression (steps a) and b)); a rewetting agglomeration (steps c) and d)) and a filtration (step e)).

BRIEF DESCRIPTION OF THE FIGURE

FIG. 1 shows a plant suitable for performing the process according to the invention.

DETAILED DESCRIPTION OF THE INVENTION

The process can be performed continuously, in which case the individual steps are performed in continuous apparatus connected in series. Alternatively, the process can be performed batchwise, in which case the individual steps are performed successively in a single apparatus, for example a stirred vessel.

First, the esterification catalyst is deactivated and precipitated by adding an aqueous base. At the same time, the acid or partial esters of the acid not converted in the esterification reaction are converted to salts. It has been found that sufficiently rapid and complete neutralization is achieved when the aqueous base is added at a temperature T of more than 100° C. under a pressure p which is equal to or greater than the vapor pressure of water at the temperature T. The raw ester which is present after the esterification reaction or after the removal of excess alcohol generally has an elevated temperature. It can be cooled if appropriate, but only to the extent that its temperature is still more than 100° C. The aqueous base is added under pressure conditions under which the water does not evaporate spontaneously. The base is therefore available for the neutralization reaction completely in dissolved liquid form.

This accelerates the reaction and allows full conversion. If the aqueous base were to be added under lower pressure, water would evaporate and the dissolved base would precipitate out in solid form. The solid base would be available for the neutralization only with a significantly lower reaction rate, if at all. In the process according to the invention, the amount of base used can be reduced, which also reduces the amount of solid to be disposed of. The formation of solid deposits on vessel walls or pipelines and blockage of the pipelines is prevented.

In general, the raw ester has a temperature T of from 120 to 185° C. The corresponding vapor pressure $p_{vap}$ of water can be taken from the table below or reference works known to those skilled in the art. The person skilled in the art is aware that the vapor pressure of solvents is influenced by dissolved substances or mixing phenomena. These influences can be neglected in the present context. For the purposes of the present invention, the emphasis is on the vapor pressure of pure water.

TABLE

| Vapor pressure of water | |
|---|---|
| T [° C.] | $p_{vap}$ [bar] |
| 105 | 1.208 |
| 110 | 1.432 |
| 115 | 1.690 |
| 120 | 1.985 |
| 125 | 2.320 |
| 130 | 2.700 |
| 135 | 3.128 |
| 140 | 3.613 |
| 145 | 4.154 |

TABLE-continued

| Vapor pressure of water | |
|---|---|
| T [° C.] | $p_{vap}$ [bar] |
| 150 | 4.758 |
| 160 | 6.179 |
| 170 | 7.917 |
| 180 | 10.026 |
| 190 | 12.549 |
| 200 | 15.547 |

In general, the pressure p at which step a) is carried out is higher than the vapor pressure $p_{vap}$ at the temperature T. The pressure p is preferably at least 1.1 times $p_{vap}$, especially at least 1.25 times $p_{vap}$. Pressures of more than 25 bar are costly and inconvenient to achieve in industry and are therefore not preferred.

The aqueous base can be added in any suitable manner. It is preferably added below the liquid surface of the raw ester. Suitable examples for this purpose are lances or nozzles which are provided on a vessel bottom or the vessel wall. The mixture is then mixed intensively, for example by means of stirrers or of a circulation pump.

In the case of continuous performance, step a) is appropriately performed by spraying the aqueous base into a stream of the raw ester. To homogeneously mix in the aqueous base, the mixed stream is conducted through at least one mixer. Useful mixers here are dynamic mixers or static mixers or combinations thereof. Static mixers are preferred. In terms of flow mechanics, the static mixers can be divided into turbulent and laminar mixers. In the case of the turbulent mixers, both free turbulence-generating mixing systems and those with internals are useful. The suitable static mixers include multiflux mixers, helical mixers, vortex mixers, gate mixers, Sulzer SMX mixers, Sulzer SMV mixers and Kenics mixers. In a suitable embodiment, the static mixer is a tube with a cross section-narrowing diaphragm. The pressure jump beyond the diaphragm generates turbulence, which leads to sufficient mixing.

The amount of aqueous base added is such that it is sufficient for complete neutralization of the acidic components of the raw ester. In practice, a greater or lesser excess of base is used. The total amount of the acidic components of the raw ester is appropriately covered by the acid number (in mg KOH/g). Preference is given to using the aqueous base to introduce from 100 to 300% neutralization equivalents, based on the acid number of the raw ester, especially from 130 to 220%. A neutralization equivalent is understood to mean the amount of base that can bind the same number of protons as 1 mg of KOH. In other words, a base excess of up to 200% is used, preferably from 30 to 120%.

Useful aqueous bases include solutions of hydroxides, carbonates, hydrogencarbonates of alkali metals and alkaline earth metals. Aqueous alkali metal hydroxide solutions are generally preferred. Aqueous sodium hydroxide solution is particularly preferred owing to its ready availability.

The concentration of the aqueous base is not critical per se, but the esters can be hydrolyzed at the introduction site of the base when concentrated alkali solutions are used. On the other hand, the concentration of the aqueous base should not be too low, since the water introduced with the aqueous base has to be removed again in the next step. Preference is therefore given to aqueous bases of moderate to low concentration, for example those of a concentration of from 0.5 to 25% by weight, especially from 1 to 10% by weight. Aqueous sodium hydroxide solution with a concentration of from 1 to 5% by weight is particularly preferred.

The ester-based mixture is kept at the pressure p for a hold time, for example from 15 seconds to 10 minutes, preferably from 30 seconds to 5 minutes. In a continuous process regime, the mixture passes, for example, through a mixing zone during the hold time.

In the next step, the ester-based mixture is decompressed, for example to a pressure of less than 800 mbar, especially less than 250 mbar, for example from 50 to 150 mbar. In this way, the water introduced with the aqueous base can be removed without excessively thermally stressing the raw ester. Owing to the decompression, the mixture separates into a liquid phase and a vapor phase. The vapor phase which is drawn off removes the water introduced with the aqueous base again. In addition to the water introduced with the aqueous base, this treatment usually also evaporates off a portion of the residue alcohol. The vapors comprising water and alcohol can be collected and condensed and discarded or sent to a reuse.

After the decompression, the liquid phase generally has a temperature of from 130 to 200° C. For this purpose, it is possible to heat the liquid phase if required.

The type of decompression vessel is not critical. For example, the mixture can be decompressed into a stirred tank in which a further treatment of the liquid phase is effected.

To complete the evaporation of the water, preference is given to mechanically moving the liquid phase obtained in the decompression under reduced pressure over a residence time of, for example, from 5 minutes to 1 hour, especially from 10 to 40 minutes. Suitable stirrers for this purpose are of various designs, for example a crossbeam stirrer.

After step b), the precipitated solid, which consists essentially of catalyst decomposition products and salts of unconverted acid or partial esters of polybasic acids, is present in finely distributed form which is difficult to filter. The process according to the invention therefore envisages measures in which the fine particles are agglomerated to larger, readily removable particles.

To this end, the liquid phase is mixed with water to form a water-in-oil emulsion. The water is distributed as a dispersed phase in the form of fine droplets in the liquid organic phase. The fine solid particles migrate to the interface between water droplets and surrounding organic phase. In the subsequent evaporation of the water, the fine particles agglomerate and form coarse, readily removable particles.

In order that a separate water phase forms, the amount of water added must be greater than corresponds to the solubility of water in the organic phase. The water solubility in the organic phase depends on factors including the content of unconverted alcohol, since the alcohol acts as a solubilizer. The higher the alcohol content, the more water has to be added in step c). In the case of typical residual alcohol contents of from 1 to 3% by weight, amounts of from 10 to 60 g of water, preferably from 20 to 40 g, based on 1 kg of raw ester are generally suitable.

The water phase is divided into fine droplets with a suitable stirrer or homogenizer. The water droplets obtained preferably have a mean particle size of less than 1000 μm. Suitable stirrers with a high specific stirrer output are, for example, disk stirrers. Alternatively, particularly in the case of a continuous process regime, it is possible to use a mixing nozzle, in which water is added directly to the raw ester stream through a dispersing valve.

Step c) is effected appropriately at about standard pressure.

In the next step, the water is distilled out again of the emulsion thus obtained. Preference is given to avoiding nucleate boiling. To this end, the emulsion can be conducted through an evaporator, for example a falling-film evaporator. Alternatively, the emulsion can be moved mechanically, for example stirred, under reduced pressure. The stirring is effected appropriately under relatively low-shear conditions. Excessive input of shear energy could divide the still-labile agglomerates of the solid catalyst residues again to undesired fine particles. Preference is given to distilling the water off at a temperature of from 60 to less than 100° C. and a pressure of less than 500 mbar. If desired, the water can also be distilled off in several steps in successive stirred vessels, in which case a lower pressure and/or a higher temperature than in the preceding step is employed in the second or further step. The transfer from a stirred vessel into the downstream stirred vessel is preferably effected under relatively low-shear conditions, for example by free overflow and not by pumped transfer. In addition to the emulsion water, a portion of the residual alcohol usually also distills off in the course of this treatment. The vapors comprising water and alcohol can be collected and condensed, and discarded or sent to a reuse.

After this treatment, the solid is present in readily filterable form; no fines get through the filtration. The use of filtration aids is not required; their use is not preferred. For filtration of the ester, all suitable filters are suitable, such as chamber filter presses, band filters, cartridge filters or pan filters. For a continuous process regime, particularly pan filters with centrifugal discarding of the filtercake are suitable. The solids removed are discarded.

After the filtration, the ester can be subjected to various aftertreatments, such as steam stripping or the like.

The raw ester used in the process according to the invention originates from a customary esterification process. Such processes are known to those skilled in the art and are described in many patent publications. In these processes, at least one carboxylic acid and/or carboxylic anhydride is reacted with an alcohol or alcohol mixture. In many cases, the alcohol serves simultaneously as an azeotroping agent for the water of reaction which forms in the reaction and is therefore used in excess. Preference is given to removing the majority of the unconverted alcohol still present here from the raw ester before step a). The alcohol content of the raw ester used in step a) is generally less than 5% by weight, for example from 1 to 3% by weight.

In the esterification process, the acid components used are carboxylic acids and/or carboxylic anhydrides. In the case of polybasic carboxylic acids, it is also possible to use partly anhydrized compounds. It is likewise possible to use mixtures of carboxylic acids and anhydrides. The acids may be aliphatic, including carbocyclic, heterocyclic, saturated or unsaturated, and aromatic, including heteroaromatic.

The suitable carboxylic acids include aliphatic monocarboxylic acids having at least 5 carbon atoms, especially from 5 to 20 carbon atoms, such as n-pentanoic acid, 2-methylbutyric acid, 3-methylbutyric acid, 2-methylpentanoic acid, 2-ethylbutyric acid, n-heptanoic acid, isoheptanoic acids, 2-methylhexanoic acid, cyclohexanecarboxylic acid, n-octanoic acid, 2-ethylhexanoic acid, isooctanoic acids, n-nonanoic acid, 2-methyloctanoic acid, isononanoic acids, n-decanoic acid, isodecanoic acids, 2-methylundecanoic acid, isoundecanoic acid, tricyclodecanecarboxylic acid and isotridecanoic acid.

Additionally suitable are aliphatic $C_4$-$C_{10}$-dicarboxylic acids or anhydrides thereof, such as maleic acid, fumaric acid, maleic anhydride, succinic acid, succinic anhydride, adipic acid, suberic acid, trimethyladipic acid, azelaic acid, decanedioic acid, dodecanedioic acid, brassylic acid. Examples of carbocyclic compounds are: hexahydrophthalic anhydride (cyclohexane-1,2-dicarboxylic anhydride), hexahydrophthalic acid (cyclohexane-1,2-dicarboxylic acid), cyclohexane-1,4-dicarboxylic acid, cyclohex-4-ene-1,2-dicarboxylic acid, cyclohexene-1,2-dicarboxylic anhydride, 4-methylcyclohexane-1,2-dicarboxylic acid, 4-methylcyclohexane-1,2-dicarboxylic anhydride, 4-methylcyclohex-4-ene-1,2-dicarboxylic acid, 4-methylcyclohex-4-ene-1,2-dicarboxylic anhydride.

Examples of suitable aromatic dicarboxylic acids or anhydrides thereof are: phthalic acid, phthalic anhydride, isophthalic acid, terephthalic acid, or naphthalenedicarboxylic acids and anhydrides thereof.

Examples of suitable aromatic tricarboxylic acids or anhydrides thereof are trimellitic acid, trimellitic anhydride or trimesic acid; examples of a suitable aromatic tetracarboxylic acid or anhydride thereof are pyromellitic acid and pyromellitic anhydride.

Particular preference is given to using phthalic anhydride or adipic acid as the carboxylic acid component.

Preference is given to using branched or linear aliphatic alcohols having from 4 to 13 carbon atoms. The alcohols are monohydric and may be secondary or primary.

The alcohols used may originate from various sources. Suitable feedstocks are, for example, fatty alcohols, alcohols from the Alfol process, or alcohols or alcohol mixtures which have been obtained by hydrogenating saturated or unsaturated aldehydes, especially those whose synthesis includes a hydroformylation step.

Alcohols which are used in the esterification process are, for example, n-butanol, isobutanol, n-octan-1-ol, n-octan-2-ol, 2-ethylhexanol, nonanols, decyl alcohols or tridecanols prepared by hydroformylation or aldol condensation and subsequent hydrogenation. The alcohols can be used as a pure compound, as a mixture of isomeric compounds or as a mixture of compounds with different carbon numbers. For example, $C_9/C_{11}$, alcohol mixtures can be used.

Preferred starting alcohols are mixtures of isomeric octanols, nonanols or tridecanols, the latter being obtainable from the corresponding butene oligomers, especially oligomers of linear butenes, by hydroformylation and subsequent hydrogenation. The preparation of the butene oligomers can in principle be carried out by three methods. Acid-catalyzed oligomerization, in which, in industry, for example, zeolites or phosphoric acid on supports are used, affords the most branched oligomers. In the case of use of linear butenes, for example, a $C_8$ fraction is formed, which consists essentially of dimethylhexenes (WO 92/13818). A process which is likewise practiced worldwide is oligomerization with soluble Ni complexes, known as the DIMERSOL process (B. Cornils, W. A. Herrmann, Applied Homogenous Catalysis with Organometallic Compounds, page 261-263, Verlag Chemie 1996). In addition, oligomerization is practiced over fixed bed nickel catalysts, for example the OCTOL process (Hydrocarbon Process., Int. Ed. (1986) 65 (2. Sect. 1), page 31-33).

Very particularly preferred feedstocks for the inventive esterification are mixtures of isomeric nonanols or mixtures of isomeric tridecanols, which are prepared by oligomerizing linear butenes to $C_8$-olefins and $C_{12}$-olefins by the Octol process, with subsequent hydroformylation and hydrogenation.

Additionally suitable are alkylene glycol monoethers, especially ethylene glycol monoethers, e.g. ethylene glycol mono-$C_1$-$C_{18}$-alkyl ethers, such as ethylene glycol monomethyl ether, ethylene glycol monoethyl ether, ethylene glycol propyl ether, ethylene glycol monobutyl ether (2-butoxyethanol) and mixtures thereof; and polyalkylene glycol monoethers, especially polyethylene glycol monoethers, such as polyethylene glycol monomethyl ether.

Particularly preferred alcohols are 2-ethylhexanol, 2-propylheptanol, isononanol isomer mixtures, decanol isomer mixtures and $C_9/C_{11}$-alcohol mixtures, and also ethylene glycol monobutyl ether.

The esterification catalyst is suitably selected from alkoxides, carboxylates and chelate compounds of titanium, zirconium, tin, aluminum and zinc. Suitable esterification catalysts are tetraalkyl titanates, such as tetramethyl titanate, tetraethyl titanate, tetra-n-propyl titanate, tetraisopropyl titanate, tetra-n-butyl titanate, tetraisobutyl titanate, tetra-sec-butyl titanate, tetraoctyl titanate, tetra(2-ethylhexyl) titanate; dialkyl titanates ($(RO)_2TiO_2$, in which R is, for example, isopropyl, n-butyl, isobutyl), such as isopropyl n-butyl titanate; titanium acetylacetonate chelates, such as diisopropoxybis(acetylacetonate)titanate, diisopropoxybis(ethylacetylacetonate)titanate, di-n-butyl-bis(acetylacetonate)titanate, di-n-butylbis(ethylacetoacetate)titanate, triisopropoxidebis(acetylacetonate)titanate; zirconium tetraalkoxides such as zirconium tetraethoxide, zirconium tetrabutoxide, zirconium tetrabutyrate, zirconium tetrapropoxide, zirconium carboxylates such as zirconium diacetate; zirconium acetylacetonate chelates, such as zirconium tetra(acetylacetonate), tributoxyzirconium acetylacetonate, dibutoxyzirconium bis(acetylacetonate); aluminum trisalkoxides, such as aluminum triisopropoxide, aluminum trisbutoxide; aluminum acetylacetonate chelates, such as aluminum tris(acetylacetonate) and aluminum tris(ethyl-acetylacetonate). In particular, isopropyl n-butyl titanate, tetra(isopropyl) orthotitanate or tetra(butyl) orthotitanate are used.

The catalyst concentration is generally from 0.005 to 1.0% by weight based on the reaction mixture, especially from 0.01 to 0.3% by weight.

The alcohol to be converted, which serves as an azeotroping agent, can be used in a stoichiometric excess, preferably from 30 to 200%, more preferably from 50 to 100%, of the amount needed in stoichiometric terms.

The esters thus prepared from polybasic carboxylic acids, for example phthalic acid, adipic acid, sebacic acid, maleic acid, and from alcohols, find wide use in coating resins, as constituents of paints and especially as plasticizers for polymers. Specific esters which can be worked up by the process according to the invention are plasticizers for PVC, such as dioctyl phthalates, diisononyl phthalates, diisodecyl phthalates and dipropylheptyl phthalates; plasticizers, for example for use in polyvinyl butyral, such as dibutyl glycol adipate, dioctyl azelate, dioctyl adipate, dibutyl sebacate, di(2-ethylhexyl) sebacate and dioctyl sebacate, and also dibutyl glycol phthalate.

The invention is illustrated in detail by the appended drawing and the examples which follow.

FIG. 1 shows a plant suitable for performing the process according to the invention. Line 1 is used to introduce the raw ester mixture with a temperature of, for example, about 150° C. and a pressure of 10 bar. Line 2 is used to meter aqueous base, for example aqueous sodium hydroxide or potassium hydroxide solution, into the ester stream. The mixture passes through a static mixer (not shown), in order to mix the aqueous base homogeneously into the raw ester stream. In order to prevent evaporation of water, a pressure is maintained in the pipeline, which is above the vapor pressure of water at the existing temperature. The residence time in the mixing zone upstream of the valve 3 is, for example, from 1 to 2 min. The valve 3 is then used to decompress the raw ester stream into the stirred tank 4. The vapor obtained in the stirred tank 4 is removed via line 5 and can be condensed and collected.

The raw ester mixture is transferred via the pump 6 and the heat exchanger 7 into the stirred tank 8. Line 9 is used to add water. Under the pressure and temperature conditions in the tank 8 (e.g. 80° C., standard pressure), the water added does not evaporate immediately and is distributed by stirring as a dispersed phase in the ester mixture in the form of small droplets. The stirrer has a high specific stirrer output and is, for example, a disk stirrer.

The emulsion passes via line 10 into the stirred tank 11 and via line 12 into the stirred tank 13. In stirred tanks 11 and 13, there exist pressure and temperature conditions (e.g. 80° C. and 100 mbar in tank 11; 80° C. and 50 mbar in tank 13), under which water and any free alcohol distill off and are removed via the draws 14 and 15 respectively. At the outlet of the tank 13, the catalyst residues are present in readily filterable solid form in the ester. The ester can be fed via the pump 16 to a filtration unit (not shown), in which the solids are filtered off.

EXAMPLES

Example 1

A stream of 6500 g/h of raw diisononyl phthalate (DINP) with an acid number of 0.2 mg KOH/g and an alcohol content of 2.4% by weight was worked up continuously.

The DINP stream with a temperature of about 145° C. was admixed under a pressure of 6 bar with 174 g/h of 1% aqueous sodium hydroxide solution (corresponding to a 90% excess, based on the acid number of the raw ester). The mixed stream passed through a mixing zone; the residence time in the mixing zone is about 1 min. The stream was then decompressed to about 100 mbar in a first stirred vessel. The residence time in the first stirred vessel was about 0.5 h, during which the mixture was stirred with a 3-level crossbeam stirrer at 160° C.

The mixture was transferred by pumping into a second stirred vessel and cooled at the same time to about 80° C. The pressure in the second stirred vessel was ambient. 130 g/h of water was added (corresponding to 2% by weight, based on the raw ester stream). The residence time in the second stirred vessel was about 0.5 h, during which the mixture was mixed intensively with a disk stirrer (specific power input: 3 W/l).

The emulsion was transferred to a third stirred vessel at a temperature of 80° C. In the third stirred vessel, the pressure was about 100 mbar. The residence time in the third stirred vessel was about 1 h, during which the mixture was stirred with a 3-level crossbeam stirrer with low stirrer output (less than 0.1 W/l). The vapors comprising water and alcohol were drawn off.

The product was collected and fed via a reservoir vessel to a pressure suction filter and filtered there through a Teflon fabric with pore size 10 μm.

This gave a clear product completely free of catalyst residues with an acid number of 0.01 mg KOH/g, an alcohol content of 1.3% by weight and a water content of 0.04% by weight. Stripping with steam reduced the alcohol content to less than 0.01% by weight.

Comparative Example

The preceding example was repeated, except that the raw ester was passed directly into the first stirred vessel and the aqueous sodium hydroxide solution was likewise metered into the first stirred vessel.

This gave a product with an acid number of 0.08 mg KOH/g. The product has a higher filter resistance compared to example 1.

The invention claimed is:

1. A process for working up a raw ester of an esterification reaction catalyzed by a metallic esterification catalyst, the process comprising
    a) admixing the raw ester with an aqueous base at a temperature T of more than 100° C. at a pressure p under which the water does not evaporate spontaneously, to form an ester-based mixture;
    b) keeping the ester-based mixture at the pressure p for a hold time of from 15 seconds to 10 minutes;
    c) decompressing the ester-based mixture and evaporating off water, to form a liquid phase;
    d) admixing the resulting liquid phase with water to form a water-in-oil emulsion,
    e) distilling water out of the emulsion, and
    f) filtering the ester.

2. The process according to claim 1, wherein step a) is performed continuously, by spraying the aqueous base into a stream of the raw ester and conducting the mixed stream through a static mixer.

3. The process according to claim 1, wherein the aqueous base is used to introduce from 100 to 300% neutralization equivalents, based on the acid number of the raw ester.

4. The process according to claim 1, wherein the aqueous base is an aqueous alkali metal hydroxide solution.

5. The process according to claim 1, wherein the concentration of the aqueous base is from 0.5 to 25% by weight.

6. The process according to claim 1, wherein the ester-based mixture is decompressed in step c) to a pressure of less than 800 mbar.

7. The process according to claim 1, wherein the liquid phase obtained in step c) is moved mechanically over a residence time of from 5 minutes to 1 hour.

8. The process according to claim 1, wherein the liquid phase in step d) is admixed with from 10 to 60 g of water based on 1 kg of raw ester.

9. The process according to claim 1, wherein water is distilled off in step e) at a temperature of from 60 to less than 100° C. and a pressure of less than 500 mbar.

10. The process according to claim 1, wherein no filtration aid is used in step f).

11. The process according to claim 1, wherein the raw ester further comprises unconverted alcohol and before step a), a majority of the unconverted alcohol is removed from the raw ester.

12. The process according to claim 1, wherein the metallic esterification catalyst comprises a compound selected from the group consisting of an alkoxide, an carboxylate and a chelate compound of titanium, zirconium, tin, aluminum and zinc.

13. The process according to claim 1, wherein the esterification reaction comprises the conversion of a carboxylic acid and/or anhydrides thereof selected from aliphatic monocarboxylic acids having at least 5 carbon atoms, aliphatic $C_4$-$C_{10}$-dicarboxylic acids, aromatic monocarboxylic acids, aromatic dicarboxylic acids, aromatic tricarboxylic acids, aromatic tetracarboxylic acids.

14. The process according to claim 1, wherein the esterification reaction comprises the conversion of an alcohol selected from $C_4$-$C_{13}$-alcohols, alkylene glycol monoethers, polyalkylene glycol monoethers and mixtures thereof.

* * * * *